(12) United States Patent
Loupis et al.

(10) Patent No.: US 9,655,829 B2
(45) Date of Patent: May 23, 2017

(54) COMPOSITIONS AND METHODS FOR TEETH WHITENING

(71) Applicant: VALEANT PHARMACEUTICALS INTERNATIONAL, INC., Bridgewater, NJ (US)

(72) Inventors: Nikolaos Loupis, Athens (GR); Remigio Piergallini, Grottammare Ascoli Piceno (IT)

(73) Assignee: VALEANT PHARMACEUTICALS INTERNATIONAL, INC., Montreal, Quebec (CA)

(*) Notice: Subject to any disclaimer, the term of this patent is extended or adjusted under 35 U.S.C. 154(b) by 0 days.

(21) Appl. No.: 15/006,943

(22) Filed: Jan. 26, 2016

(65) Prior Publication Data
US 2016/0136075 A1 May 19, 2016

Related U.S. Application Data

(62) Division of application No. 14/018,393, filed on Sep. 4, 2013, now abandoned.

(60) Provisional application No. 61/701,354, filed on Sep. 14, 2012.

(51) Int. Cl.
| | |
|---|---|
| A61K 8/49 | (2006.01) |
| A61K 8/42 | (2006.01) |
| A61K 8/22 | (2006.01) |
| A61Q 11/00 | (2006.01) |
| A61N 5/06 | (2006.01) |

(52) U.S. Cl.
CPC ............... *A61K 8/498* (2013.01); *A61K 8/22* (2013.01); *A61K 8/42* (2013.01); *A61Q 11/00* (2013.01); *A61K 2800/42* (2013.01); *A61K 2800/434* (2013.01); *A61K 2800/48* (2013.01); *A61K 2800/52* (2013.01); *A61K 2800/81* (2013.01); *A61N 5/062* (2013.01); *A61N 2005/0606* (2013.01)

(58) Field of Classification Search
USPC .......................................................... 424/53
See application file for complete search history.

(56) References Cited

U.S. PATENT DOCUMENTS

| | | |
|---|---|---|
| 2,877,221 A | 3/1959 | Lanbach |
| 3,293,127 A | 12/1966 | Beck |
| 3,372,125 A | 3/1968 | Hill |
| 3,595,798 A | 7/1971 | Smith et al. |
| 3,652,420 A | 3/1972 | Hill |
| 3,728,446 A | 4/1973 | Roberts et al. |
| 4,574,097 A | 3/1986 | Honeycutt |
| 4,846,165 A | 7/1989 | Hare et al. |
| 4,891,211 A | 1/1990 | Winston |
| 4,992,256 A | 2/1991 | Skaggs et al. |
| 5,658,148 A | 8/1997 | Neuberger |
| 5,749,968 A | 5/1998 | Melanson et al. |
| 5,785,527 A | 7/1998 | Jensen et al. |
| 5,844,016 A | 12/1998 | Sawhney et al. |
| 5,858,332 A | 1/1999 | Jensen et al. |
| 5,922,331 A | 7/1999 | Mausner |
| 5,977,199 A | 11/1999 | Xie |
| 6,030,222 A | 2/2000 | Tarver |
| 6,036,493 A | 3/2000 | Sharma |
| 6,056,548 A | 5/2000 | Neuberger et al. |
| 6,084,005 A | 7/2000 | Fukunishi et al. |
| 6,107,466 A | 8/2000 | Hasan et al. |
| 6,121,341 A | 9/2000 | Sawhney et al. |
| 6,149,895 A | 11/2000 | Kutsch |
| 6,162,055 A | 12/2000 | Montgomery et al. |
| 6,254,388 B1 | 7/2001 | Yarborough |
| 6,267,976 B1 | 7/2001 | Barnhart et al. |
| 6,337,357 B1 | 1/2002 | Fukunishi et al. |
| 6,343,933 B1 | 2/2002 | Montgomery et al. |
| 6,361,329 B1 | 3/2002 | Dekker et al. |
| 6,365,134 B1 | 4/2002 | Orlowski et al. |
| 6,387,353 B1 | 5/2002 | Jensen et al. |
| 6,391,283 B1 | 5/2002 | Jensen et al. |
| 6,420,455 B1 | 7/2002 | Landgrebe et al. |
| 6,423,697 B1 | 7/2002 | Friedman |
| 6,440,396 B1 | 8/2002 | McLaughlin |
| 6,444,725 B1 * | 9/2002 | Trom ................... A61K 6/0017 522/25 |
| 6,475,497 B1 | 11/2002 | Rajaiah et al. |
| 6,485,709 B2 | 11/2002 | Banerjee et al. |
| 6,488,914 B2 | 12/2002 | Montgomery |

(Continued)

FOREIGN PATENT DOCUMENTS

| | | |
|---|---|---|
| AU | 2011245008 A1 | 12/2012 |
| BR | PI0618475 | 8/2011 |

(Continued)

OTHER PUBLICATIONS

Alster et al. "Photodynamic Therapy: Practical Cosmetic Applications" 2006, *J. of Drugs in Dermatology* 5(8):764-768 (XP 008147410).
Antunes et al. "Evaluation of the Clastogenicity and Anticlastongenicity of the Carotenoid Bixin in Human Lymphocyte Cultures" 2005, Mutat. Res. 585(1-2):113-119.
Berneburg et al. "Phototherapy with Narrowband UVB" 2005, *Acta Derm Venereol*. 85(2):98-108.
Coleman et al. "The Healing of Wounds in the Skin of Piglets Treated with Benzoyl Peroxide" 1978, *J. Dermatol. Surg. Oncol.* 4(9)/705-707 (XP 009151883).
Darzynkiewicz et al. "Photosensitizing Effects of the Tricyclic Heteroaromatic Cationic Dyes Pyronin Y and Toluidine Blue O (Toloniium Chloride)" Mar. 1, 1988, Cancer Res. 48(5):1295-1299.
De et al. "Environmental Effects on the Aggregation of Some Xanthese Dyes Used in Lasers" 2005) Spectrochim Acta A Mol. Biomol. Spectrosc 61(8):1821-1833.

(Continued)

*Primary Examiner* — Walter Webb
(74) *Attorney, Agent, or Firm* — Pepper Hamilton LLP

(57) ABSTRACT

Disclosed herein are teeth whitening compositions generally including an oxidizing agent, and an activating agent that has an emission wavelength between about 400 nm and about 570 nm. Methods of employing these compositions to whiten teeth, methods of making these compositions and kits that include some or part of the composition ingredients, are also described.

16 Claims, 8 Drawing Sheets

(56) References Cited

U.S. PATENT DOCUMENTS

| | | |
|---|---|---|
| 6,514,543 B2 | 2/2003 | Montgomery |
| 6,528,555 B1 | 3/2003 | Nikutowski et al. |
| 6,536,628 B2 | 3/2003 | Montgomery |
| 6,541,460 B2 | 4/2003 | Petito |
| 6,558,653 B2 | 5/2003 | Andersen et al. |
| 6,846,182 B1 | 1/2005 | Sibner |
| 6,905,672 B2 | 6/2005 | Rajaiah et al. |
| 6,960,079 B2 | 11/2005 | Brennan et al. |
| 7,114,953 B1 | 10/2006 | Wagner |
| 7,220,438 B2 | 5/2007 | Quintanilla Almagro et al. |
| 7,314,470 B2 | 1/2008 | Malodobry |
| 7,354,448 B2 | 4/2008 | Altshuler et al. |
| 8,075,875 B2 | 12/2011 | Piergallini et al. |
| 8,334,328 B2 | 12/2012 | Marmarinos et al. |
| 8,414,911 B2 | 4/2013 | Mattson et al. |
| 8,632,822 B2 | 1/2014 | Piergallini et al. |
| 8,637,086 B2 | 1/2014 | Piergallini et al. |
| 8,658,219 B2 | 2/2014 | Piergallini et al. |
| 8,685,466 B2 | 4/2014 | Piergallini et al. |
| 8,986,719 B2 | 3/2015 | Piergallini et al. |
| 2001/0022970 A1 | 9/2001 | Dees et al. |
| 2002/0197214 A1 | 12/2002 | Bublewitz et al. |
| 2003/0133940 A1 | 7/2003 | Dees et al. |
| 2003/0134932 A1 | 7/2003 | Lehmann et al. |
| 2003/0162760 A1 | 8/2003 | Masatsuji et al. |
| 2003/0198605 A1 | 10/2003 | Montgomery |
| 2004/0028624 A1 | 2/2004 | Bublewitz et al. |
| 2004/0097627 A1 | 5/2004 | Vallittu et al. |
| 2004/0136971 A1 | 7/2004 | Scharp et al. |
| 2004/0191330 A1 | 9/2004 | Keefe et al. |
| 2005/0020696 A1 | 1/2005 | Montgomery et al. |
| 2005/0026298 A1 | 2/2005 | Bickett et al. |
| 2005/0049228 A1 | 3/2005 | Albrecht et al. |
| 2005/0059731 A1 | 3/2005 | Albrecht et al. |
| 2005/0100514 A1 | 5/2005 | Sakaguchi et al. |
| 2005/0123588 A1 | 6/2005 | Zhu et al. |
| 2005/0124721 A1 | 6/2005 | Arthur et al. |
| 2005/0124722 A1 | 6/2005 | Arthur et al. |
| 2005/0249677 A1 | 11/2005 | Malcmacher et al. |
| 2006/0099155 A1 | 5/2006 | MacDonald et al. |
| 2006/0198796 A1 | 9/2006 | Giniger et al. |
| 2006/0287211 A1 | 12/2006 | Barbizan et al. |
| 2007/0092469 A1 | 4/2007 | Jacobs |
| 2007/0128132 A1* | 6/2007 | Piergallini ............... A61K 8/22 424/53 |
| 2007/0148623 A1 | 6/2007 | Dias et al. |
| 2007/0166369 A1 | 7/2007 | Neuberger et al. |
| 2007/0244195 A1 | 10/2007 | Burkhart et al. |
| 2008/0108681 A1 | 5/2008 | Scimeca et al. |
| 2008/0113037 A1 | 5/2008 | Green et al. |
| 2008/0206159 A1 | 8/2008 | Tamarkin et al. |
| 2008/0305101 A1 | 12/2008 | Ruoslahti et al. |
| 2009/0238778 A1 | 9/2009 | Mordas et al. |
| 2009/0269121 A1 | 10/2009 | Snedden et al. |
| 2010/0152296 A1 | 6/2010 | Marmarinos et al. |
| 2010/0266989 A1 | 10/2010 | Piergallini et al. |
| 2011/0027753 A1 | 2/2011 | Maurat et al. |
| 2011/0218482 A1 | 9/2011 | Piergallini et al. |
| 2011/0224599 A1 | 9/2011 | Piergallini et al. |
| 2012/0095455 A1 | 4/2012 | Rodmond et al. |
| 2012/0171641 A1 | 7/2012 | Piergallini et al. |
| 2012/0237580 A1 | 9/2012 | Piergallini et al. |
| 2013/0122467 A1 | 5/2013 | Piergallini et al. |
| 2014/0105832 A1 | 4/2014 | Loupis et al. |

FOREIGN PATENT DOCUMENTS

| | | |
|---|---|---|
| BR | PI0720819-7 | 12/2012 |
| CA | 2222027 A1 | 6/1998 |
| CA | 2551613 A1 | 12/2005 |
| CA | 2580381 A1 | 1/2006 |
| CA | 2632187 A1 | 5/2008 |
| CA | 2677468 A1 | 8/2008 |
| CA | 2797867 A1 | 11/2011 |
| CN | 101340887 | 1/2009 |
| CN | 101594904 | 12/2009 |
| CN | 101677908 | 3/2010 |
| CN | 102939072 | 2/2013 |
| EP | 0356868 A2 | 3/1990 |
| EP | 0380157 A1 | 8/1990 |
| EP | 0704539 A2 | 4/1996 |
| EP | 1235543 A | 9/2002 |
| EP | 1235544 A | 9/2002 |
| EP | 1749532 A1 | 2/2007 |
| EP | 1779891 A1 | 5/2007 |
| EP | 1951184 B1 | 8/2008 |
| EP | 2111213 A | 10/2009 |
| EP | 2563323 A | 3/2011 |
| EP | 2338465 A1 | 6/2011 |
| JP | 01-279838 | 11/1989 |
| JP | 02-233612 | 9/1990 |
| JP | H03-169805 | 7/1991 |
| JP | 04-219756 | 8/1992 |
| JP | H10-182390 A | 7/1998 |
| JP | H10-330235 A | 12/1998 |
| JP | 2000-053550 | 2/2000 |
| JP | 2001-511137 | 8/2001 |
| JP | 2002-502864 | 1/2002 |
| JP | 2002/226349 | 8/2002 |
| JP | 2002-293747 A | 10/2002 |
| JP | 2003-339875 A | 12/2003 |
| JP | 2009-514943 | 4/2009 |
| JP | 2012-229229 | 11/2012 |
| KR | 10-2010-0004934 | 1/2010 |
| MX | 2012012481 | 3/2013 |
| SG | 184945 A1 | 11/2012 |
| WO | WO 81/00513 A1 | 3/1981 |
| WO | WO 90/09779 A1 | 9/1990 |
| WO | WO 91/02530 A1 | 7/1991 |
| WO | WO 97/21420 A1 | 6/1997 |
| WO | WO 98/10738 A1 | 3/1998 |
| WO | WO 98/11827 A1 | 3/1998 |
| WO | WO 98/23219 A1 | 6/1998 |
| WO | WO 98/30169 A1 | 7/1998 |
| WO | WO 98/33761 A1 | 8/1998 |
| WO | WO 98/36700 A1 | 8/1998 |
| WO | WO 99/39238 A1 | 8/1999 |
| WO | WO 99/40870 A1 | 8/1999 |
| WO | WO 99/49823 A1 | 10/1999 |
| WO | WO 99/63900 A1 | 12/1999 |
| WO | WO 01/00190 A2 | 1/2001 |
| WO | WO 01/12181 A1 | 2/2001 |
| WO | WO 02/22097 A1 | 3/2002 |
| WO | WO 02/087642 A2 | 11/2002 |
| WO | WO 03/000215 A1 | 1/2003 |
| WO | WO 03/017824 A2 | 3/2003 |
| WO | WO 03/061696 A2 | 7/2003 |
| WO | WO 03/099247 A1 | 12/2003 |
| WO | WO 2004/028498 A1 | 4/2004 |
| WO | WO 2004/073540 A2 | 9/2004 |
| WO | WO 2004/081222 A2 | 9/2004 |
| WO | WO 2005/009604 A1 | 2/2005 |
| WO | WO 2005/051305 A2 | 6/2005 |
| WO | WO 2006/014597 A1 | 2/2006 |
| WO | WO 2006/032847 A1 | 3/2006 |
| WO | WO 2006/047868 A1 | 5/2006 |
| WO | WO 2006/772243 A1 | 7/2006 |
| WO | WO 2006/125650 A1 | 11/2006 |
| WO | WO 2006/135344 A1 | 12/2006 |
| WO | WO 2007/025244 A2 | 3/2007 |
| WO | WO 2007/080453 A2 | 7/2007 |
| WO | WO 2008/011707 A1 | 1/2008 |
| WO | WO 2008/013962 A2 | 1/2008 |
| WO | WO 2008/096182 A1 | 8/2008 |
| WO | WO 2009/089345 A2 | 7/2009 |
| WO | WO 2010/051636 A1 | 5/2010 |
| WO | WO 2010/051641 A1 | 5/2010 |
| WO | WO 2010/145696 A1 | 12/2010 |
| WO | WO 2011/006263 A1 | 1/2011 |
| WO | WO 2011/058448 A2 | 5/2011 |
| WO | WO 2011/134087 A1 | 11/2011 |

(56) References Cited

FOREIGN PATENT DOCUMENTS

| WO | WO 2012/126120 A1 | 9/2012 |
|---|---|---|
| WO | WO 2013/155620 A1 | 10/2013 |
| WO | WO 2014/042936 A2 | 3/2014 |

OTHER PUBLICATIONS

European Search Report and Written Opinion for EP06849243 mailed Sep. 20, 2007.
European Search Report and Written Opinion for EP11161795 dated May 23, 2011.
European Search Report and Written Opinion for EP2563323 dated Aug. 4, 2011.
FDA Product Classification Database Search, Device: Eosin y: database updated Jun. 6, 2008.
FDA, Color Additive Status List: http://www.cfsan.fda.gov/opa-appc.html Dec. 2009.
Fischersci "Material Safety Data Sheet: Sodium Acetate Buffer" Apr. 13, 2000 (Revised Jan. 7, 2005, https://fscimage.fishersci.com/msds/91502.htm.
Goldberg "Photodynamic Therapy in Skin Rejuvenation" 2008, Clinics in Dermatology 26(6):608-613 (XP 25545890).
International Search Report and Written Opinion for PCT/CA2011/050261 mailed Aug. 4, 2011.
International Search Report and Written Opinion for PCT/CA2012/050177 mailed Jun. 28, 2012.
International Search Report and Written Opinion for PCT/GR2007/000006 mailed Oct. 12, 2007.
International Search Report and Written Opinion for PCT/IB2006/004034 mailed Sep. 20, 2007.
Jankowski et al. "The action of photosensitizers and Serum in a Bactericidal Process. II. The Effects of Dyes: Hypericin, Eosin Y and Saphranine O" 2005, Pol. J. Microbiol. 54(4):323-330.
Kelly et al. "Combined Photodynamic and Photothermal Induced Injury Enhances Damage to in vivo Model Blood Vessels" 2004, Lasers in Surgery and Medicine 34(5):407-413 (XP 008147412).

McCullach et al. "Photosensitized Destruction of Chlorella Vulgaris by Methylene Blue or Nuclear Fast Red Combined with Hydrogen Peroxide Under Visible Light Irradiation" 2006, Environ. Sci. Tech. 40:2421-2425.
Meisel et al. "Photocynamic Therapy for Periodontal Diseases: State of the Art" 2005, Journal of Photochemistry and Photobiology B:Biology 79:159-170.
Montenegro et al. "Model Studies on the Photosensitized Isomerication of Bixin" 2004, J. Agric Food Chem. 52(2):367-373.
Nolan et al. "The efficacy of Topical Hyaluronic Acid in the Management of Oral Lichen Planus" Feb. 23, 2009, Journal of Oral Pathology and Medicine 38(3):299-303.
Publication date of following document established by Internet Archive Wayback Machine<URL: <http://web.archive.org/web/20090208211504/http://en.widipedia.org/wiki/Eosin , Feb. 8, 2009.
Rao et al. "Photocatalytic Transformation of Dyes and By-products in the Presence of Hydrogen Peroxide" 2003, Environ. Technol. 24(8):1025-1030 (abstract only).
Rodgers, Fluorescence Polarization Standards for High-Throughput Screening and Imaging 2002, BioTechniques 32:34-42.
Roy et al. "Dermal Wound Healing is Subject to Redox Control" 2006, Mol. Ther. 13(1):211-220 (XP 005197711).
Sezer et al. "Topical Drug Delivery Using Chitosan Nano- and Microparticles" 2012, Informa UK (ISSN 1742-5247) pp. 1129-1146 (abstract only).
Steinberg et al. "Genetic and Physiological Effects of Noncoherent Visible Light Combined with Hydrogen Peroxide on *Streptococcus mutans* in Biofilm" Mar. 3, 2008, Antimicrobial Agents and Chemotherapy 52(7):2626-2631.
Subba et al. "Photocatalytic Transformation of Dyes and By-Products in teh Presence of Hydrogen Perixide" 2003, Environ. Technol. 24(8):1025-1030.
Sun "Lasers and Light Amplification in Dentistry" retrieved online at http://www.sundds.com/laser/ on Jun. 23, 2005

\* cited by examiner

COMPOSITIONS AND METHODS FOR TEETH WHITENING

CROSS-REFERENCE TO RELATED APPLICATIONS

This application is a divisional of U.S. patent application Ser. No. 14/018,393, entitled "Compositions and Methods for Teeth Whitening" and filed Sep. 4, 2013, which claims the priority benefit of U.S. Provisional Application No. 61/701,354, entitled "Compositions and Methods for Whitening Teeth" and filed Sep. 14, 2012, both of which are hereby incorporated by reference in their entireties.

BACKGROUND OF THE DISCLOSURE

Various agents such as certain foods and tobacco, the process of aging, diseases, trauma, medications, some congenital conditions, and environmental effects can cause teeth to become discolored. Because white or whitened teeth are usually considered to be cosmetically desirable, there is a great deal of interest in developing compositions and methods for whitening teeth.

Peroxide and peroxyacid compounds, such as hydrogen peroxide and carbamide peroxide, are useful as bleaching agents in teeth whitening compositions. Appropriate heat, light, or chemical sources can accelerate the release of oxygen radicals from the peroxide or peroxyacid compounds.

Tooth sensitivity following treatment, and the time required for teeth whitening compositions (typically requiring about an hour of time or multiple applications or both), however, remains a significant drawback.

This application is directed to improvements in tooth whitening compositions and also provides kits and methods of using the same.

SUMMARY

The present disclosure provides compositions for teeth whitening comprising an oxidizing agent and at least one chromophore. In some aspects, the present disclosure provides a composition comprising an oxidizing agent and Eosin Y and Fluorescein. In other aspects, present disclosure provides a composition comprising an oxidizing agent and Eosin Y, Fluorescein and Rose Bengal. In other aspects, the present disclosure provides a composition comprising an oxidizing agent and Eosin Y and Rose Bengal. In other aspects, the present disclosure provides a composition comprising an oxidizing agent and Fluorescein and Rose Bengal. In other aspects, the present disclosure provides a composition comprising an oxidizing agent and Eosin Y, Fluorescein and Erythrosine.

In certain embodiments of any of the foregoing or following, the oxidizing agent comprises hydrogen peroxide or carbamide peroxide or both. In certain embodiments, the hydrogen peroxide content is less than or equal to 6% by weight of hydrogen peroxide in the composition. In other aspects, the carbamide peroxide content is less than or equal to 22% by weight of carbamide peroxide in the composition. In other aspects, the total content of the oxidizing agent is equivalent to about 6% by weight of hydrogen peroxide content.

In certain embodiments of any of the foregoing or following, the composition further comprises a stabilizing agent.

In certain embodiments of any of the foregoing or following, the composition further comprises a thickening agent. In certain embodiments, the thickening agent comprises silicon dioxide and/or fumed silica having a particle size less than one micron.

In certain embodiments of any of the foregoing or following, the composition further comprises a hydrophilic gelling agent. In certain embodiments, the hydrophilic gelling agent comprises polypropylene glycol, polyethylene glycol, propylene glycol, glycerol, or a large molecular weight polyol, or any combination thereof.

In certain embodiments of any of the foregoing or following, the composition further comprises a base. In some embodiments, the base comprises potassium hydroxide.

In certain embodiments of any of the foregoing or following, the pH of the composition is between 2 and 10. In other embodiments, the pH of the composition is between 4 and 8, preferably between 6 and 7, more preferably 6.5.

In certain embodiments of any of the foregoing or following, Eosin Y is present in an amount of 0.001% to 1% weight per weight of the composition.

In certain embodiments of any of the foregoing or following, Fluorescein is present in an amount of 0.001% to 1% weight per weight of the composition.

In certain embodiments of any of the foregoing or following, Rose Bengal is present in an amount of 0.001% to 1% weight per weight of the composition.

In certain embodiments of any of the foregoing or following, Erythrosin is present in an amount of 0.001% to 1% weight per weight of the composition.

In further aspects, the present disclosure provides kits for preparing and/or applying any of the compositions of the present disclosure. In some embodiments, the kit comprises a first component comprising an oxidizing agent; and a second component comprising Eosin Y and Fluorescein. In other embodiments, the kit comprises a first component comprising an oxidizing agent; and second component comprising Eosin Y, Fluorescein and Rose Bengal. In other embodiments, the kit comprises a first component comprising an oxidizing agent and a second component comprising Eosin Y and Rose Bengal. In other embodiments, the kit comprises a first component comprising an oxidizing agent and a second component comprising Fluorescein and Rose Bengal. In other embodiments, the kit comprises a first component comprising an oxidizing agent and a second component comprising Eosin Y, Fluorescein and Erythrosine.

In certain embodiments, the first and second components additionally comprise a hydrophilic gelling agent.

In certain embodiments, the kit additionally comprises an applicator comprising a tooth brightening composition. In certain embodiments, the kit additionally comprises a gingival barrier composition. In some embodiments, the kit further comprises instructions for using the kit, apparatus for mixing together the first and second components, a light source, or information for assessing the efficacy of the composition.

The present disclosure also provides a method for whitening teeth comprising applying a composition of the disclosure to at least one tooth and exposing the composition applied to the at least one tooth to actinic light.

In some embodiments, each tooth is exposed to actinic light for about 1-30 seconds. In other embodiments, each tooth is exposed to actinic light for about 3-10 seconds. In other embodiments, each tooth is exposed to the actinic light for about 5-10 seconds.

DETAILED DESCRIPTION

(1) Definitions

Figure 1:
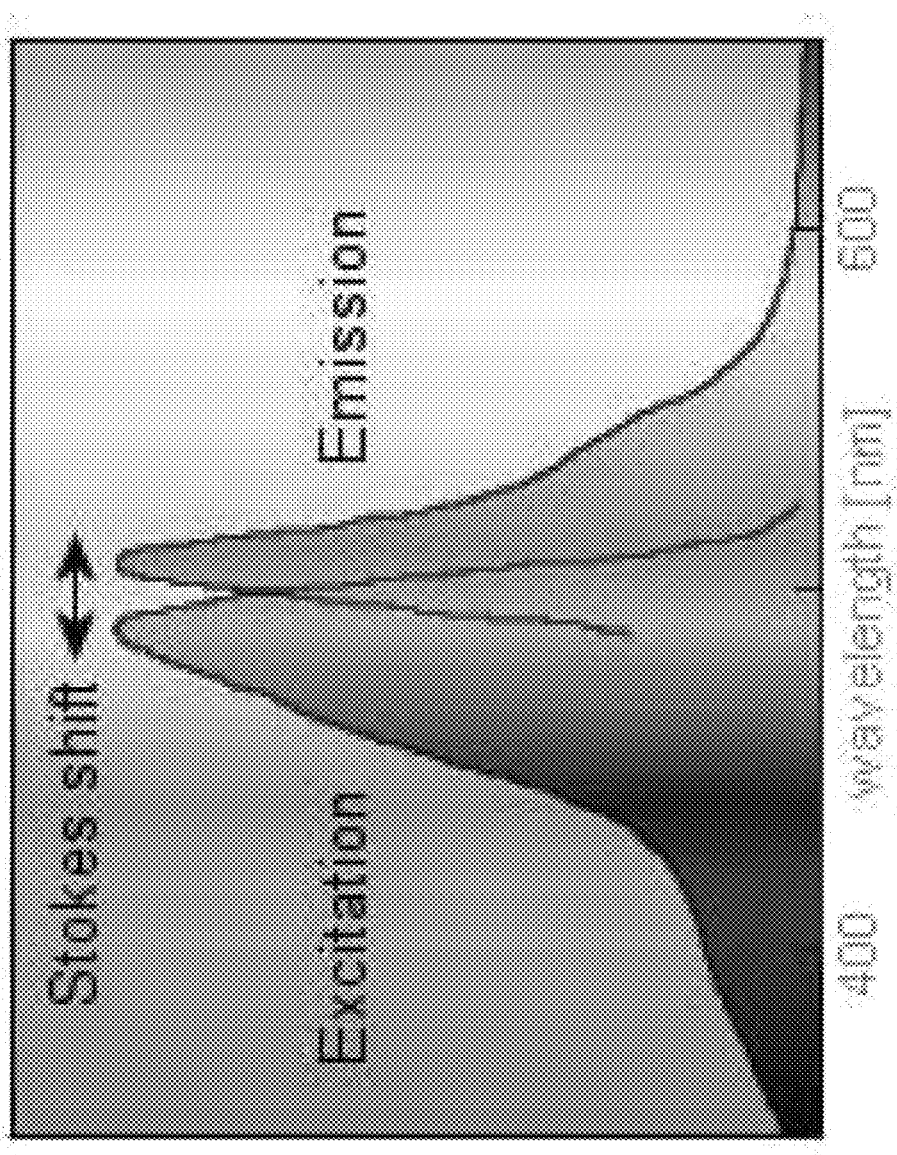
FIG. 1 illustrates the Stokes' shift.

Before continuing to describe the present disclosure in further detail, it is to be understood that this disclosure is not limited to specific compositions or process steps, as such may vary. It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 10%, and more preferably within 5% of the given value or range.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The term "accelerating agent" refers to any agent capable of accelerating and/or contributing to the completion of radical generation.

The term "actinic light" is intended to mean light energy emitted from a specific light source (e.g. lamp, LED, or laser) and capable of being absorbed by matter (e.g. the chromophore or photoactivator defined below). In a preferred embodiment, the actinic light is visible light.

The term "photosensitive agent" refers to any agent capable of absorbing actinic light. The photosensitive agent undergoes photoexcitation and transfers its energy. This may be in the form of emitted light (e.g. fluorescence) and/or energy transferred to molecules. This energy may initiate chemical reactions. Photosensitive agents may enhance and/or accelerate the dispersion of light energy, or otherwise enhance and/or activate the decomposition of an oxidizing agent.

The terms "photosensitive agent", "chromophore", "photosensitizing agent", "photosensitizer", "photoactivating agent" and "photoactivator" are used herein interchangeably. A chromophore means a chemical compound or a part of a chemical compound, which when contacted by light irradiation, is capable of absorbing the light. The chromophore readily undergoes photoexcitation and then emits energy such as by transferring its energy to other molecules or by emitting light.

"Gelling agent" means an agent that thickens and stabilizes liquid solutions, emulsions and suspensions.

"Oxidant" or "oxidizing agent", which terms are used interchangeably herein, means a chemical compound that readily transfers oxygen atoms and oxidizes other compounds and also includes precursors of compounds capable of oxidizing other compounds.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature and not as restrictive, and the full scope of the subject matter is set forth in the claims.

(2) Tooth Whitening Compositions

The present disclosure provides compositions for teeth whitening.

In some aspects, the present disclosure provides a composition comprising an oxidizing agent and a photosensitive agent (e.g., comprising one or more chromophores), which, when activated by light, disperses the light energy, leading to the photochemical activation of the oxidant contained in the composition, which may lead to the formation of oxygen radicals, such as singlet oxygen.

In other aspects, the present disclosure provides a first composition and a second composition, wherein the first composition comprises an oxidizing agent and the second composition comprises a photosensitive agent (e.g., comprising one or more chromophores), which, when mixed with the first composition and subsequently activated by light, disperses the light energy, leading to the photochemical activation of the oxidant contained in the mixture, which may lead to the formation of oxygen radicals, such as singlet oxygen.

In further aspects, the present disclosure provides a composition or compositions comprising a photosensitive agent (e.g. comprising one or more chromophores), which when exposed to light, can be activated to initiate chemical reactions. When the composition or compositions are applied to teeth, it can react with oxidizing species in, on, or applied to, the teeth, to have a teeth whitening effect.

In yet further aspects, the present disclosure provides a composition or compositions comprising a photosensitive agent, said photosensitive agent comprising at least two chromophores having a synergistic effect together. The at least chromophores can be activated on exposure to light to initiate chemical reactions. When the composition is applied to teeth, the chemical reactions may include oxidizing species in, on, or applied to, the teeth, to have a teeth whitening effect.

The compositions of the present disclosure may be described based on the components making up the composition. Additionally or alternatively, the compositions of the present disclosure have functional and structural properties and these properties may also be used to define and describe the compositions. Individual components of the composition of the present disclosure are detailed as below.

Photosensitive Agents

The compositions of the present disclosure may comprise one or more photosensitive agents, e.g., chromophores. The term "chromophore" (used herein interchangeably with "photosensitizing agent", or "photosensitizer" or "photoactivator") is intended to mean a part or whole of a chemical compound capable of absorbing actinic light. The chromophore readily undergoes photoexcitation and may then transfer its energy to other molecules. The energy transferal may also be in the form of emitted light or fluorescence.

Suitable chromophores can be fluorescent dyes (or stains), although other dye groups or dyes (biological and histological dyes, food colorings, carotenoids) can also be used. Combining chromophores may increase photo-absorption by the combined dye molecules and enhance absorption and photo-biomodulation selectivity. This creates multiple possibilities of generating new photosensitive, and/or selective chromophores mixtures. Thus, in certain embodiments, compositions of the disclosure include more than one photoactivator.

In certain embodiments, a composition of the present disclosure comprises a first chromophore which undergoes at least a partial photobleaching upon application of light. By photobleaching is meant a photochemical destruction of the chromophore which can generally be visualized as a loss of colour.

In some embodiments, the first chromophore absorbs at a wavelength in the range of the visible spectrum, such as at a wavelength of about 380-800 nm, 380-700, or 380-600 nm. In other embodiments, the first chromophore absorbs at a wavelength of about 200-800 nm, 200-700 nm, 200-600 nm or 200-500 nm. In one embodiment, the first chromophore absorbs at a wavelength of about 200-600 nm. In some embodiments, the first chromophore absorbs light at a wavelength of about 200-300 nm, 250-350 nm, 300-400 nm, 350-450 nm, 400-500 nm, 450-650 nm, 600-700 nm, 650-750 nm or 700-800 nm.

Figure 2:
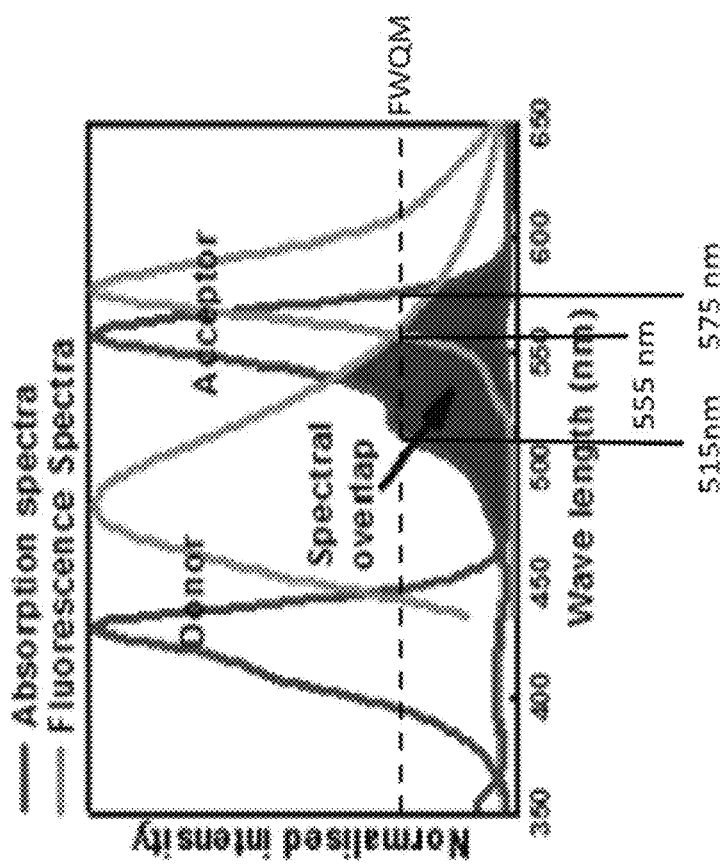
FIG. 2 illustrates the absorption and emission spectra of donor and acceptor chromophores. The spectral overlap between the absorption spectrum of the acceptor chromophore and the emission spectrum of the donor chromophore is also shown.

The compositions disclosed herein may also include at least one additional chromophore. When such multichromophore compositions are illuminated with light, energy transfer can occur between the chromophores. This process, known as resonance energy transfer, is a photophysical process through which an excited 'donor' chromophore (also referred to herein as first chromophore) transfers its excitation energy to an 'acceptor' chromophore (also referred to herein as second chromophore). The efficiency and directedness of resonance energy transfer depends on the spectral features of donor and acceptor chromophores. In particular, the flow of energy between chromophores is dependent on a spectral overlap reflecting the relative positioning and shapes of the absorption and emission spectra. More specifically, for energy transfer to occur, the emission spectrum of the donor chromophore must overlap with the absorption spectrum of the acceptor chromophore (FIG. 2).

Figure 3:
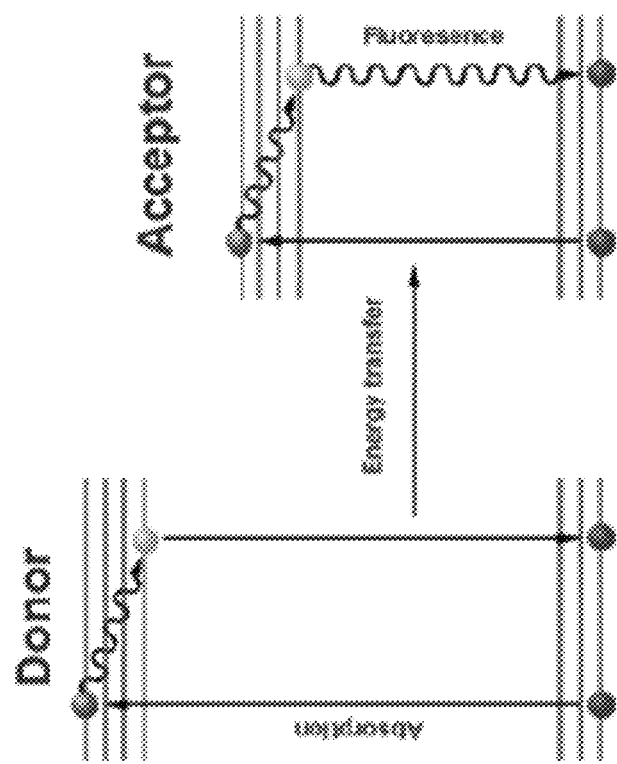
FIG. 3 is a schematic of a Jablonski diagram that illustrates the coupled transitions involved between a donor emission and acceptor absorbance.

Energy transfer manifests itself through decrease or quenching of the donor emission and a reduction of excited state lifetime accompanied also by an increase in acceptor emission intensity. FIG. 3 is a Jablonski diagram that illustrates the coupled transitions involved between a donor emission and acceptor absorbance.

To enhance the energy transfer efficiency, the donor chromophore should have good abilities to absorb photons and emit photons. Furthermore, the more overlap there is between the donor chromophore's emission spectra and the acceptor chromophore's absorption spectra, the better a donor chromophore can transfer energy to the acceptor chromophore.

When more than one chromophore is included, the first chromophore may have an emission spectrum that overlaps at least about 80%, 50%, 40%, 30%, 20% or 10% with an absorption spectrum of the second chromophore. In some embodiments, the first chromophore has an emission spectrum that overlaps at least about 20% with an absorption spectrum of the second chromophore. In further embodiments, the first chromophore has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second chromophore.

% spectral overlap, as used herein, means the % overlap of a donor chromophore's emission wavelength range with an acceptor chromophore's absorption wavelength rage, measured at spectral full width quarter maximum (FWQM). For example, FIG. 2 shows the normalized absorption and emission spectra of donor and acceptor chromophores. The spectral FWQM of the acceptor chromophore's absorption spectrum is from about 60 nm (515 nm to about 575 nm). The overlap of the donor chromophore's spectrum with the absorption spectrum of the acceptor chromophore is about 40 nm (from 515 nm to about 555 nm). Thus, the % overlap can be calculated as 40 nm/60 nm×100=66.6%.

In some embodiments, the second chromophore absorbs at a wavelength in the range of the visible spectrum. In certain embodiments, the second chromophore has an absorption wavelength that is relatively longer than that of the first chromophore within the range of about 50-250, 25-150 or 10-100 nm.

It will be appreciated that the compositions of the present disclosure may include, in addition to a first and second chromophore, a third, fourth, etc. chromophore. In compositions including three chromophores, not only is there spectral overlap between the emission spectrum of the first chromophore and the absorption spectrum of the second chromophore, spectral overlap also exists between the emission spectrum of the second chromophore and the absorption spectrum of the third chromophore. In some aspects, the second chromophore has an emission spectrum that overlaps at least about 20% with an absorption spectrum of the third chromophore. In some embodiments, the second chromophore has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the third chromophore.

In compositions including four chromophores, not only is there spectral overlap between the emission/absorption spectra of the first, second and third chromophores, spectral overlap also exists between the emission spectrum of the third chromophore and the absorption spectrum of the fourth chromophore. In some aspects, the third chromophore has an emission spectrum that overlaps at least about 20% with an absorption spectrum of the fourth chromophore. In some embodiments, the third chromophore has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the fourth chromophore.

As discussed above, the application of light to the compositions of the present disclosure results in a cascade of energy transfer between the chromophores. In certain embodiments, such a cascade of energy transfer provides photons that penetrate the dental tissue. In some embodiments, such a cascade of energy transfer is not accompanied by concomitant generation of heat. In some other embodiments, the cascade of energy transfer does not result in tissue damage such as damage to the enamel of a tooth.

In some embodiments, the photosensitive agent or agents not only are capable of emitting light in the wavelength range from about 400 nm to about 570 nm, but also absorb light in the wavelength range from about 400 nm to about 570 nm. Such a photosensitive agent is activated by light in the wavelength range of from about 400 nm to about 570 nm. Accordingly, in one embodiment the photosensitive agent absorbs light in the wavelength range of about 400 nm to about 570 nm. In another embodiment, the photosensitive agent absorbs light at a wavelength between about 470 nm to about 550 nm. This embodiment therefore allows for the optimal absorption of energy from the actinic light and the optimal transmission through dentin and enamel.

Without wishing to be bound to any particular theory, it is also believed that photosensitive agents of the present disclosure, when exposed to actinic light, can accelerate the dispersion of light energy which consequently leads to a complete photochemical activation of the oxidizing agent within the composition. It is believed that a gel mass can transmit light in the wavelength range of about 400 nm to about 570 nm, so that when a photosensitive agent in the gel mass is exposed to actinic light, the dispersion of the light energy leads to an accelerated photochemical activation of the peroxide. Together, these embodiments allow for favourable absorption by the photosensitive agent of energy from the actinic light and the favourable transmission through the composition, dentin and enamel.

Suitable chromophores that may be used as photosensitive agents in the tooth whitening compositions of the present disclosure include, but are not limited to, chlorophyll dyes, xanthenes dyes, methylene blue dyes and azo dyes.

Exemplary chlorophyll dyes include but are not limited to chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Exemplary xanthene dyes include but are not limited to Eosin B (4',5'-dibromo,2',7'-dinitr-o-fluorescein, dianion); eosin Y; eosin Y (2',4',5',7'-tetrabromo-fluorescein, dianion); eosin (2',4',5',7'-tetrabromo-fluorescein, dianion); eosin (2',4',5',7'-tetrabromo-fluorescein, dianion) methyl ester; eosin (2',4',5',7'-tetrabromo-fluorescein, monoanion) p-isopropyl-benzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tribromo-fluorescein, dianion); eosin derivative (2',4',5',7'-tetrachlor-o-fluorescein, dianion); eosin; eosin dicetylpyridinium chloride ion pair; erythrosin B (2',4',5',7'-tetraiodo-fluorescein, dianion); erythrosin; erythrosin dianion; erythiosin B; fluorescein; fluorescein dianion; phloxin B (2',4',5',7'-tetrabromo-3,4,5,6-tetrachloro-fluorescein, dianion); phloxin B (tetrachloro-tetrabromo-fluorescein); phloxine B; rose bengal (3,4,5,6-tetrachloro-2',4',5',7'-tetraiodo-fluorescein, dianion); pyronin G, pyronin J, pyronin Y; Rhodamine dyes such as rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Exemplary methylene blue derivatives include but are not limited to 1-methyl methylene blue; 1,9-dimethyl methylene blue; methylene blue; methylene blue (16 μM); methylene blue (14 μM); methylene violet; bromomethylene violet; 4-iodomethylene violet; 1,9-dimethyl-3-dimethyl-amino-7-diethyl-a-mino-phenothiazine; and 1,9-dimethyl-3-diethyl-amino-7-dibutyl-amino-phenot-hiazine.

Exemplary azo (or diazo-) dyes include but are not limited to methyl violet, neutral red, para red (pigment red 1), amaranth (Azorubine S), Carmoisine (azorubine, food red 3, acid red 14), allura red AC (FD&C 40), tartrazine (FD&C Yellow 5), orange G (acid orange 10), Ponceau 4R (food red 7), methyl red (acid red 2), and murexide-ammonium purpurate.

In some aspects of the disclosure, the one or more chromophores of the tooth whitening composition disclosed herein can be independently selected from any of Acid black 1, Acid blue 22, Acid blue 93, Acid fuchsin, Acid green, Acid green 1, Acid green 5, Acid magenta, Acid orange 10, Acid red 26, Acid red 29, Acid red 44, Acid red 51, Acid red 66, Acid red 87, Acid red 91, Acid red 92, Acid red 94, Acid red 101, Acid red 103, Acid roseine, Acid rubin, Acid violet 19, Acid yellow 1, Acid yellow 9, Acid yellow 23, Acid yellow 24, Acid yellow 36, Acid yellow 73, Acid yellow S, Acridine orange, Acriflavine, Alcian blue, Alcian yellow, Alcohol soluble eosin, Alizarin, Alizarin blue 2RC, Alizarin carmine, Alizarin cyanin BBS, Alizarol cyanin R, Alizarin red S, Alizarin purpurin, Aluminon, Amido black 10B, Amidoschwarz, Aniline blue WS, Anthracene blue SWR, Auramine O, Azocannine B, Azocarmine G, Azoic diazo 5, Azoic diazo 48, Azure A, Azure B, Azure C, Basic blue 8, Basic blue 9, Basic blue 12, Basic blue 15, Basic blue 17, Basic blue 20, Basic blue 26, Basic brown 1, Basic fuchsin, Basic green 4, Basic orange 14, Basic red 2, Basic red 5, Basic red 9, Basic violet 2, Basic violet 3, Basic violet 4, Basic violet 10, Basic violet 14, Basic yellow 1, Basic yellow 2, Biebrich scarlet, Bismarck brown Y, Brilliant crystal scarlet 6R, Calcium red, Carmine, Carminic acid, Celestine blue B, China blue, Cochineal, Coelestine blue, Chrome violet CG, Chromotrope 2R, Chromoxane cyanin R, Congo corinth, Congo red, Cotton blue, Cotton red, Croceine scarlet, Crocin, Crystal ponceau 6R, Crystal violet, Dahlia, Diamond green B, Direct blue 14, Direct blue 58, Direct red, Direct red 10, Direct red 28, Direct red 80, Direct yellow 7, Eosin B, Eosin Bluish, Eosin, Eosin Y, Eosin yellowish, Eosinol, Erie garnet B, Eriochrome cyanin R, Erythrosin B, Ethyl eosin, Ethyl green, Ethyl violet, Evans blue, Fast blue B, Fast green FCF, Fast red B, Fast yellow, Fluorescein, Food green 3, Gallein, Gallamine blue, Gallocyanin, Gentian violet, Haematein, Haematine, Haematoxylin, Helio fast rubin BBL, Helvetia blue, Hematein, Hematine, Hematoxylin, Hoffman's violet, Imperial red, Ingrain blue, Ingrain blue 1, Ingrain yellow 1, INT, Kermes, Kermesic acid, Kernechtrot, Lac, Laccaic acid, Lauth's violet, Light green, Lissamine green SF, Luxol fast blue, Magenta 0, Magenta I, Magenta II, Magenta III, Malachite green, Manchester brown, Martius yellow, Merbromin, Mercurochrome, Metanil yellow, Methylene azure A, Methylene azure B, Methylene azure C, Methylene blue, Methyl blue, Methyl green, Methyl violet, Methyl violet 2B, Methyl violet 10B, Mordant blue 3, Mordant blue 10, Mordant blue 14, Mordant blue 23, Mordant blue 32, Mordant blue 45, Mordant red 3, Mordant red 11, Mordant violet 25, Mordant violet 39 Naphthol blue black, Naphthol green B, Naphthol yellow S, Natural black 1, Natural red, Natural red 3, Natural red 4, Natural red 8, Natural red 16, Natural red 25, Natural red 28, Natural yellow 6, NBT, Neutral red, New fuchsin, Niagara blue 3B, Night blue, Nile blue, Nile blue A, Nile blue oxazone, Nile blue sulphate, Nile red, Nitro BT, Nitro blue tetrazolium, Nuclear fast red, Oil red O, Orange G, Orcein, Pararosanilin, Phloxine B, Picric acid, Ponceau 2R, Ponceau 6R, Ponceau B, Ponceau de Xylidine, Ponceau S, Primula, Purpurin, Pyronin B, Pyronin G, Pyronin Y, Rhodamine B, Rosanilin, Rose bengal, Saffron, Safranin O, Scarlet R, Scarlet red, Scharlach R, Shellac, Sirius red F3B, Solochrome cyanin R, Soluble blue, Solvent black 3, Solvent blue 38, Solvent red 23, Solvent red 24, Solvent red 27, Solvent red 45, Solvent yellow 94, Spirit soluble eosin, Sudan III, Sudan IV, Sudan black B, Sulfur yellow S, Swiss blue, Tartrazine, Thioflavine S, Thioflavine T, Thionin, Toluidine blue, Toluyline red, Tropaeolin G, Trypaflavine, Trypan blue, Uranin, Victoria blue 4R, Victoria blue B, Victoria green B, Water blue I, Water soluble eosin, Xylidine ponceau, or Yellowish eosin.

In some embodiments, the composition includes Eosin Y as a first chromophore and Fluorescein as a second chromophore. It is believed that the combination of Eosin Y and Flurorescein has a synergistic effect. It is further believed that because Eosin Y and Fluorescein reemit green light, that this green light can and may be further absorbed (or reabsorbed) by the chromophores so that light energy is not dissipated as in conventional compositions. This absorbed and re-emitted light is thought to penetrate throughout the whitening composition, and also to be transmitted into the enamel and dentin.

In other embodiments, the composition includes Eosin Y as a first chromophore, fluorescein as a second chromophore, and Rose Bengal as a third chromophore. It is believed that the combination of Eosin Y, Fluorescein and Rose Bengal also has a synergistic effect.

In further embodiments, the composition includes Eosin Y and Rose Bengal; Fluorescein, Eosin Y and Erythrosine B; Fluorescein and Rose Bengal; Rose Bengal and Erythrosine B; Fluorescein and Erythrosine B. Other synergistic chromophore combinations are also possible.

By means of synergistic effects of the chromophore combinations in the composition, the light absorption and emission amounts may be increased, and the time to absorb and emit light energy reduced. Advantageously, this may translate to increased reactivity of the composition and faster teeth whitening. Also, by means of the synergistic chromophore combinations, the amount of oxidizing agent in the compositions can be lowered, or even avoided, without compromising the efficacy of the composition. Also, the treatment conditions need not be altered to achieve the same or better whitening results, such as time of exposure to light, power of light source used, wavelength of light used. In other words, use of synergistic combinations of chromophores in the final composition may allow the same or better whitening effects to be achieved using less oxidizing agent in the composition, and without necessitating a longer time of exposure to a light source or a higher power light source.

Advantageously, a lowered oxidizing agent content may be associated with decreased gum and tooth sensitivity, decreased dehydration of the tooth, decreased brittleness of the enamel, decreased decalcification of the enamel and longer lasting tooth whitening effects. The content of oxidizing agents such as hydrogen peroxide in teeth whitening compositions are also relevant from a regulatory perspective. For example, levels above 6% are not permitted by the European Commission (European Cosmetics Directive 76/768/EEC and European Cosmetic Regulation EC 1223/2009). Therefore, the use of 6% or less hydrogen peroxide, or a hydrogen peroxide equivalent, can be achieved by means of compositions of the present disclosure without compromising teeth whitening effects or necessitating longer treatment times.

In certain embodiments, the composition of the present disclosure includes any of the chromophores listed above, or a combination thereof to promote tooth whitening.

The chromophores can be included in a gel, powder, or liquid.

This is a distinct application of these agents and differs from the use of chromophores as simple stains or as a catalyst for photo-polymerization.

Oxidants (or Oxidizing Agent)

The compositions of the disclosure may include an oxidant. Oxidants are chemical compounds that readily transfer oxygen atoms and oxidizes other compounds and also include precursors of compounds capable of oxidizing other compounds. Useful oxidizing agents that may be utilized in the compositions of the present disclosure preferably include peroxide, an alkali metal percarbonate, an alkali metal perborate, or a peroxyacid known in the art. Such oxidizing agents include, but are not limited to, hydrogen peroxide, carbamide peroxide, calcium peroxide, magnesium peroxide, zinc peroxide, sodium percarbonate, potassium percarbonate, potassium persulfate, sodium persulfate, ammonium persulfate, disodium monoperphosphate, dipotassium monoperphosphate, peroxyacids, magnesium monoperoxyphthalate, sodium perborate, chlorine dioxide, and sodium chlorite. Oxidants can be provided in powder, liquid or gel form.

Oxidants may be inherent in the environment of the teeth and/or contacted with the compositions of the disclosure on application of the composition to the teeth or oral environment. In some embodiments, oxidants can be applied to the teeth (teeth 'pre-conditioning') before application of present compositions including chromophores.

Gelling Agent

The compositions of the disclosure may also include a gelling agent, such as a hydrophilic gelling agent.

In some embodiments, the nature of the gelling agent (e.g., its hydrophilic nature) prevents vaporization of the gel when exposed to actinic light, thus improving hydration of the coated tooth area. Increased hydration of the teeth and surrounding tissues is associated with decreased discomfort and sensitivity. In one embodiment, the gelling agent can include, for example, one or more modified starches and/or glucose. In some embodiments, the gelling agent further enhances the consistency of the composition, facilitating the application to the tooth surface.

Advantageously, the gelling agent can enhance the translucency or transparency upon addition to the composition and/or upon activation by, e.g., actinic light, emitted light and/or heat. In one embodiment, it minimizes vaporization of the composition. Additionally or alternatively, the gelling and/or translucency agent minimizes any thermal effects by absorbing any heat generated in the composition.

The gelling agent may be selected from any of synthetic or semi-synthetic polymeric materials, polyacrylate copolymers, cellulose derivatives and polymethyl vinyl ether/maleic anhydride copolymers. In some embodiments, the gelling agent is a hydrophilic, high molecular weight (i.e., molar masses of more than about 5,000, and in some instances, more than about 10,000, or 100,000, or 1,000, 000) and/or cross-linked polyacrylic acid polymer. In some embodiments, the gelling composition comprises a gelling agent this is a polyacrylic acid polymer has a viscosity in the range of about 20,000-100,000, 25,000-90,000, 30,000-80,000, 30,000-70,000, 30,000-60,000, 25,000-40,000 cP. In certain embodiment, the gelling agent is a hydrophilic, high molecular weight, and/or cross-linked polyacrylic acid polymer, where the polyacrylic acid polymer has a viscosity in the range of about 20,000-80,000 cP.

In some embodiments, the gelling agent comprises a carbomer. Carbomers are synthetic high molecular weight polymer of acrylic acid that are crosslinked with either allylsucrose or allylethers of pentaerythritol having a molecular weight of about $3\times10^6$. The gelation mechanism depends on neutralization of the carboxylic acid moiety to form a soluble salt. The polymer is hydrophilic and produces sparkling clear gels when neutralized. Carbomer gels possess good thermal stability in that gel viscosity and yield value are essentially unaffected by temperature. Carbomer gels possess optimum rheological properties. The inherent pseudoplastic flow permits immediate recovery of viscosity when shear is terminated and the high yield value and quick break make it ideal for dispensing. Aqueous solution of Carbopol® is acidic in nature due to the presence of free carboxylic acid residues. Neutralization of this solution cross-links and gelatinizes the polymer to form a viscous integral structure of desired viscosity.

Carbomers are available as fine white powders which disperse in water to form acidic colloidal suspensions (a 1% dispersion has approx. pH 3) of low viscosity. Neutralization of these suspensions using a base, for example sodium, potassium or ammonium hydroxides, low molecular weight amines and alkanolamines, results in the formation of clear translucent gels. Nicotine salts such as nicotine chloride form stable water-soluble complexes with carbomers at about pH 3.5 and are stabilized at an optimal pH of about 5.6.

In one embodiment of the disclosure, the carbomer is Carbopol. Such polymers are commercially available from B.F. Goodrich under the designation Carbopol® 420, 430, 475, 488, 493, 910, 934, 934P, 971P NF, 974P NF, 980 NF, 981 NF and the like. Carbopols are versatile controlled-release polymers, as described by Brock (Pharmacotherapy, 14:430-7 (1994)) and Durrani (Pharmaceutical Res. (Supp.) 8:S-135 (1991)), and belong to a family of carbomers which are synthetic, high molecular weight, non-linear polymers of acrylic acid, crosslinked with polyalkenyl polyether. In some embodiments, the carbomer is Carbopol® 974P NF, 980 NF, 5984 EP, ETD 2020 NF, Ultrez 10 NF, 934 NF, 934P NF or 940 NF. In certain embodiments, the carbomer is Carbopol® 980 NF, ETD, 2020 NF, Ultrez 10 NF, or 940 NF.

Additional Agents

The compositions of the present disclosure may also include a stabilizing agent. In some embodiments, the stabilizing agent stabilizes the peroxide concentration in the composition for days, weeks, months, a year or several years. In some embodiments, the stabilizing agent not only stabilizes the oxidizing agent, but also is a pH modifier and/or stabilizer. In some embodiments, the stabilizing agent is sodium acetate. In one embodiment, sodium acetate is added until the desired pH is attained. In one embodiment, the stabilizing agent is selected from the group consisting of antioxidants such as sodium sulfite, metal chelators (e.g., EDTA), and stabilizers (e.g., tin salts, phosphoric acid, and tin sulphonates). In some embodiments, the stabilizing agent scavenges or otherwise isolates or removes from solution, metal ions that can potentially destabilize the oxidizing agent.

In one embodiment, the pH of the composition is in or adjusted to the range of from about 4 to about 10. In alkaline conditions, with a pH from about 8 to about 10, the stronger free radical, perhydroxyl ions, can be generated. Perhydroxyl free radicals are capable of reacting not only with yellow and brown stains but even with grey chromophores situated deeper in the tooth structure. In further embodiments, the pH of the composition is between about 5 and about 7, or between about 5 and about 6, or between about 6 and 7. In certain embodiments the pH is about 6 or 6.5.

Suitable pH adjusting agents include, but are not limited to, sodium hydroxide, potassium hydroxide, ammonium hydroxide, sodium carbonate, potassium carbonate, TRIS, and triethanolamine, or any other salt of an alkaline base which is safely used in the mouth. In another embodiment, the pH adjusting agent is sodium perborate. In certain embodiments of the disclosure, a single component may act as a pH adjusting agent or as a stabilizing agent or may serve both functions. In one embodiment, sodium acetate acts as a pH adjusting agent and as a stabilizing agent. In further embodiments, the pH adjusting agent is of the group consisting of sodium bicarbonate, calcium bicarbonate, sodium carbonate and calcium carbonate.

Additionally or alternatively, the composition can include a thickening agent to improve the ease of application of the composition to the teeth such that even and effective coverage is more readily achieved. Suitable thickening agents include but are not limited to mixed silica-aluminum oxides, triethanolamine (e.g., Trolamine), and water soluble poly (ethylene oxide) resins (e.g., Polyox™). Suitable thickening agents also include amide starches.

It has been found that using a thickening agent which has a particle size in the range from about 0.2 microns (µm) to about 0.7 µm provides for more widespread dispersion of the oxidizing agent on the particle surface. Accordingly, in one embodiment, the photosensitive agent has a particle size below about 2 microns or below about 1 micron. In other embodiments, the agent has a particle size below about 0.8, 0.7, 0.6, 0.5, 0.4, 0.3, or 0.2 microns. In other embodiments, the photosensitive agent has a particle size between about 0.1 and about 0.8, between about 0.2 and about 0.7, or between about 0.3 and about 0.6 microns.

Additionally or alternatively, the thickening agent can include fumed silica and/or any other inert inorganic material that may be used as a carrier and can aid in the delivery of active oxygen to the tooth surface. Fumed silica of a small particle size (e.g., between about 0.2 microns and about 0.4 microns), can provide efficient dispersion of hydrogen peroxide and reflection of light energy within the oxidizing composition.

In some embodiments, the compositions of the disclosure include a reaction accelerator or accelerating agent. In one embodiment, the composition includes sodium perborate. Sodium perborate has selective reactivity with hydrogen peroxide in forming free radicals (reacts with water to release hydrogen peroxide). The use of one or more photosensitive agents (e.g., sodium perborate) can be advantageous because they can absorb and retain heat generated in the composition by, e.g., actinic light, thus restricting any such heat to the gel in order to accelerate the reaction without heating the tooth, which can cause sensitivity. In addition, acceleration of the reaction means that the composition can be removed more quickly than conventional compositions thereby decreasing exposure of the patient to the composition and resulting sensitivity and/or other damage to tissues and teeth.

(3) Methods of Use

Another aspect of the disclosure provides methods for tooth whitening including applying a tooth whitening composition of the present disclosure to at least one tooth, and exposing the tooth whitening composition to actinic light to activate the oxidizing agent and/or the chromophore. The composition may be any of the compositions described herein.

The method for whitening the teeth may be performed in a dentist's office or clinic under ordinary conditions. The composition can be mixed chair-side and applied to the surface of as many teeth as are desired to be whitened. The whole or part of the teeth may be treated. Alternatively, the composition can be provided without the need for mixing chair-side. For example, in a light-proof container to minimize activation of the chromophores. Thereafter, the composition can be exposed to actinic light to accelerate decomposition of the oxidizing agent and the formation of free radicals. Premixes can be prepared with some or all of the ingredients and then mixed chair-side and applied to the teeth. For example, a carbamide peroxide gel premix and a chromophore gel premix can be prepared and stored. The user then mixes the two premixes immediately prior to use. Additionally or alternatively, some or all of the remaining ingredients can also be separately premixed and stored. Such premixes can be stored, e.g., for at least about one year.

The compositions of the disclosure can be used to whiten teeth discolored by any agent or disorder. For example, the compositions may be used to whiten discoloration due to stains (e.g., tobacco, coffee, tea and/or food stains), fluorosis, developmental disturbances, bacteria, genetics, tetracycline antibiotics, trauma, blood decomposition, pigments present during development of teeth, etc. Therefore, there is also provided use of a composition of the present disclosure to whiten teeth.

In the methods of the present disclosure, any source of actinic light can be used to activate the oxidizing agent. Any type of halogen, LED or plasma arc lamp, or laser may be suitable. The primary characteristic of suitable sources of actinic light will be that they emit light in a wavelength (or wavelengths) appropriate for photosensitive the one or more photoactivators present in the composition. In one embodiment, an argon laser is used. In another embodiment, a potassium-titanyl phosphate (KTP) laser (e.g. a Green-Light™ laser) is used. In yet another embodiment, a LED photocuring device is the source of the actinic light. In yet another embodiment, the source of the actinic light is a source of light having a wavelength between about 200 to 600 nm. In another embodiment, the source of the actinic light is a source of visible light having a wavelength between about 400 and 600 nm. Furthermore, the source of actinic light should have a suitable power density.

The most intense fluorescence (e.g., emission) from a chromophore occurs when it is irradiated with wavelengths close to the peak of the absorption wavelength (i.e., excitation curve). Accordingly, in one embodiment, the actinic light is at a wavelength of about the absorption wavelength of the photosensitive agent. In one embodiment, the actinic light has a wavelength in the range from about 470 nm to about 550 nm. In another embodiment, the actinic light has a wavelength in the range from about 470 nm to about 520 nm. In a further embodiment, the actinic light has a wavelength of about 530 nm to about 535 nm.

In one embodiment, the teeth are exposed to actinic light for a total of less than 20 minutes, in another for less than 10 minutes, in another for less than 5 minutes. In one embodiment the teeth are exposed to actinic light for less than 4, 3, 2, or 1 minute. In one embodiment, the disclosure provides a method for whitening teeth at least 2 shades in about 1 minute. In some embodiments, there is no significant post-treatment sensitivity. In other embodiments, there is no post-treatment sensitivity. In yet other embodiments, the whitening effect does not diminish over time following treatment.

In one embodiment, the tooth whitening composition is applied and the tooth is exposed to multiple applications of actinic light, for a time of about 4 to about 6 seconds for each tooth per exposure. In some embodiments, the tooth is exposed to actinic light at least two, three, four, five or six times. In some embodiments, a fresh application of the tooth whitening composition is applied before each exposure to actinic light. In some embodiments, the total exposure to actinic light is less than about one minute. In other embodiments, the total exposure to actinic light is less than about 60, 40, 30, or 20 seconds.

In one embodiment, the tooth is whitened at least 7 shades, 6 shades, 5 shades, 4 shades, 3 shades, 2 shades or 1 shade. Shades can be determined before and after treatment using any of a number of shade guides, including, e.g., the VITA® (Vita Zahnfabrik H. Rauter GmbH & Co., KG), CHROMASCOP® (Ivoclar Vivadent, Inc.) or BIODENT (Dentsply Intenational) shade guides. Optionally, a shade taking system, e.g., the ShadeEye NCC Dental Chroma Meter, can be employed to determine shade before and/or after treatment.

In one embodiment, the tooth is whitened at least two shades, three shades, four shades, five shades, six shades or seven shades in less than about one minute of total exposure time to actinic light. In some embodiments, the tooth is whitened at least two shades, three shades, four shades, five shades, six shades or seven shades in less than about 40 seconds of total exposure time to actinic light. In some embodiments, the tooth is whitened at least two shades, three shades, four shades, five shades, six shades or seven shades in less than about 30 seconds of total exposure time to actinic light. In some embodiments, the tooth is whitened at least two shades, three shades, four shades, five shades, six shades or seven shades in less than about 20 seconds or even less than about 10 seconds of total exposure time to actinic light.

In one embodiment, the risk of transient inflammation of the pulp by percolation of the oxidizing agent is reduced, not significant and/or eliminated. Without wishing to be bound by any particular theory, inflammation of the pulp is thought to be caused by percolation of the oxidizing agent into the pulp tissue. In some embodiments, the synergistic effect of the photosensitive agents, and the actinic light results in an instantaneous and complete photochemical reaction. Accordingly, exposure of the tooth, the pulp, and/or the surrounding tissues to the oxidizing agent and/or other components in the composition is dramatically reduced.

In yet another aspect, the disclosure provides a method for tooth whitening comprising application of actinic light and a composition of the disclosure (any of the compositions described herein) to at least one tooth such that the tooth is whitened at least about two shades in less than about 10 minutes. In another embodiment, the tooth is whitened at least about two shades in less than about 5 minutes, less than about 4 minutes, less than about 3 minutes, less than about 2 minutes or in about 1 minute. In some embodiments, the teeth are whitened at least about 3 shades, 4 shade or 5 shades. In some embodiments, there is no significant post-treatment sensitivity or no post-treatment sensitivity.

(4) Kits

The present disclosure also provides kits for preparing and/or applying any of the compositions of the present disclosure. The kit may include a composition comprising an oxidizing agent and at least one chromophore having an emission wavelength between about 400 nm and about 570 nm. The oxidizing agent may be present in an amount of about 0.01%-40%, 0.01%-1.0%, 0.5%-10.0%, 5%-15%, 10%-20%, 15%-25%, 20%-30%, 15.0%-25%, 20%-30%, 25%-35%, or 30%-40% by weight to weight of the composition. The chromophore may be present in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In embodiments where the composition comprises more than one chromophore, the first chromophore may be present in an amount of about 0.05-40% per weight of the composition, and a second chromophore may be present in an amount of about 0.05-40% per weight of the composition. In certain embodiments, the first chromophore is present in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the second chromophore is present in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the amount of chromophore or combination of chromophores may be in the amount of about 0.05-40.05% per weight of the composition. In certain embodiments, the amount of chromophore or combination of chromophores may be in the amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40.05% per weight of the composition.

In some embodiments, the kit includes more than one composition, for example, a first and a second composition. The first composition may include the oxidizing agent and the second composition may include the chromophore having an emission wavelength between about 400 nm and about 570 nm. The oxidizing agent may be present in the first composition in an amount of about 0.01%-1.0%, 0.5%-10.0%, 5%-15%, 10%-20%, 15%-25%, 20%-30%, 15.0%-25%, 20%-30%, 25%-35%, 30%-40% or 35%-45% by weight to weight of the first composition. The chromophore may be present in the second composition in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the second composition. In embodiments where the second composition comprises more than one chromophore, the first chromophore may be present in an amount of about 0.05-40% per weight of the second composition, and a second chromophore may be present in an amount of about 0.05-40% per weight of the second composition. In certain embodiments, the first chromophore is present in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, or 35-40% per weight of the second composition. In certain embodiments, the second chromophore is present in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the second composition. In certain embodiments, the amount of chromophore or combination of chromophores may be in the amount of about 0.05-40.05% per weight of the second composition. In certain embodiments, the amount of chromophore or combination of chromophores may be in the amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40.05% per weight of the second chromophore.

In some embodiments, the kit includes containers comprising the compositions of the present disclosure. In some embodiments, the kit includes a first container comprising a first composition that includes the oxidizing agent, and a second container comprising a second composition that includes at least one chromophore. The containers may be light impermeable, air-tight and/or leak resistant. Exemplary containers include, but are not limited to, syringes, vials, or pouch. When a first composition and a second composition are included in the kit, it may be advantageous to provide the compositions in double-barrel syringes, including a mixer tip. The two compositions can then be dispensed and instantaneously mixed as the compositions exit the syringe.

A kit of the disclosure may also include directions for application. Additionally or alternatively, the kit can include apparatus for application (e.g., brushes or trays or both). The kit can also include charts or other information helpful in assessing the whitening effect desired and/or achieved by the methods and compositions of the disclosure. The kit may also include a source of actinic light. The kit may also include a retractor for the lips, mouth, cheeks in order to expose the teeth for the treatment.

A kit of the disclosure may also include an applicator or a dispenser containing a tooth brightening composition. The tooth brightening composition may be used to pre-treat the teeth before the whitening treatment and/or to treat the teeth after the whitening treatment. The tooth brightening composition may include a low concentration of an oxidizing agent, such as hydrogen peroxide. The applicator may conveniently be substantially pen-shaped, and configured to include a reservoir containing the brightening composition in fluid communication with an applicator tip for delivering the brightening composition to the teeth. An example of a tooth brightening device and composition is further described in PCT/CA2012/50177 filed 22 Mar. 2012, the contents of which are herein incorporated by reference.

Identification of equivalent compositions, methods and kits are well within the skill of the ordinary practitioner and would require no more than routine experimentation, in light of the teachings of the present disclosure. Practice of the disclosure will be still more fully understood from the following examples, which are presented herein for illustration only and should not be construed as limiting the disclosure in any way.

Identification of equivalent compositions, methods and kits are well within the skill of the ordinary practitioner and would require no more than routine experimentation, in light of the teachings of the present disclosure. Practice of the disclosure will be still more fully understood from the following examples, which are presented herein for illustration only and should not be construed as limiting the disclosure in any way.

EXAMPLES

In the forgoing examples, some amounts such as, but not limited to percentage weights or gram amounts of materials comprising the compositions, kits and methods disclosed herein may have been rounded to the nearest whole number, nearest $1/10^{th}$, nearest $1/100^{th}$, nearest $1/1,000^{th}$ or nearest $1/10,000$.

Example 1

Preparation of an Exemplary Whitening Composition

A chromophore gel premix comprising Eosin Y (0.88 mg/100 g) and Fluorescein (0.29 mg/100 g) (Table 1) was combined with an oxidizing premix including 22% of an oxidizing agent (Table 2). Approximately 2.175 g of the chromophore gel premix was mixed with approximately 9.81 g of the oxidizing pre-mix, to form the teeth whitening composition. The amount of Eosin Y in the final composition was about 0.016%, and the amount of Fluorescein was about 0.005%. The pH of the final teeth whitening composition was about 5.50 to 6.50.

TABLE 1

Chromophore gel pre-mix

| Material Name | % weight in pre-mix |
| --- | --- |
| Water | 23.33 |
| EDTA | 0.700 |
| Carbopol ultrez 10NF | 1.250 |
| Glycerin | 57.500 |
| Propylene Glycol | 15.525 |
| Methylparaben | 0.1063 |
| Propylparaben | 0.0563 |
| Potassium hydroxide | 1.42 |
| Eosin Y (D&C red 22) | 0.088 |
| Fluorescein (D&C Yellow 8) | 0.029 |

TABLE 2

Oxidizing pre-mix

| Material Name | % weight in pre-mix |
| --- | --- |
| Carbamide peroxide | 22% |

Other ingredients: Propylene glycol, ethanol, glycerin, carbomer (homopolymer), triethanolamine, peppermint essential oil.

Example 2

Preparation of an Exemplary Whitening Composition

Further whitening compositions (A to H) were prepared in the same manner as Example 1, by mixing a chromophore gel pre-mix with an oxidizing pre-mix. The oxidizing pre-mix was as shown in Table 2 above. The chromophore gel pre-mixes largely corresponded to those of Table 1, differing only in the amounts of the chromophores used (Table 3). On exposure to actinic light, all of the whitening compositions fluoresced (emitted light) and photobleached indicating a teeth whitening effect.

TABLE 3 amounts of Eosin Y and Fluorescein in different chromophore gel pre-mixes
% by weight in pre-mix

| | A | B | C | D | E | F | G | H |
| --- | --- | --- | --- | --- | --- | --- | --- | --- |
| Eosin Y | 0.166 | 0.2068 | 0.2480 | 0.2179 | 0.1737 | 0.2275 | 0.2730 | 0.1034 |
| Fluorescein | 0.166 | 0.1370 | 0.1103 | 0.1103 | 0.1103 | 0.1233 | 0.0980 | 0.0685 |

Example 3

The teeth whitening composition of Example 1 was applied to the upper and lower teeth of eight patients, covering the central incisors, lateral incisors, canines and pre-molars. A gingival barrier was applied to the gums. The teeth were then exposed for approximately three to five minutes (5-10 seconds per tooth) with a blue light (dental curing light) to activate the composition on the teeth. The activated composition was then removed. Four (4) successive applications of the composition and light exposure were performed on each patient. The shades of the treated teeth were then evaluated using Vita Shade assessment, before and immediately after the procedure. The results are summarized in Table 3. Whitening of the teeth by at least 6 shades was observed in all of the patients. None of the patients noticed gum or teeth sensitivity during or after the procedure.

TABLE 4

| | Pre-treatment | Post Treatment | Shade Variance |
| --- | --- | --- | --- |
| Patient 1 | A3 | A1 | −8 |
| Patient 2 | C2 | B1 | −7 |
| Patient 3 | A3 | D2 | −6 |
| Patient 4 | C1 | B1 | −6 |
| Patient 5 | C1 | B1 | −6 |
| Patient 6 | D3 | A2 | −6 |
| Patient 7 | C1 | B1 | −6 |
| Patient 8 | A4 | D3 | −6 |

Example 4

The whitening effect of the composition of Example 1 was evaluated on 6 patients having discoloured teeth due to tetracycline antibiotics. One patient had severe tetracycline staining, 3 had moderate staining and 2 had mild staining.

The composition of Example 1 was applied to the teeth of each patient. The teeth were then exposed to blue dental light for approximately 5-10 seconds per tooth. The activated composition was removed, and new composition applied to the teeth. This was repeated for a total of 4 cycles of composition application and light exposure. The shades of the treated teeth were then evaluated using Vita Shade® assessment, before and immediately after the procedure. Whitening of the teeth by at least 6 shades was observed in all of the patients. None of the patients noticed gum or teeth sensitivity during or after the procedure.

Example 5

The continuation of the whitening effect of the composition of Example 1 on 6 patients was evaluated 14 days, 1 month and 2 months post-treatment. The whitening composition was applied as in Examples 1 and 3. No change in the shade of the teeth was observed according to Vita Shade® evaluation.

Example 6

Figure 4A:
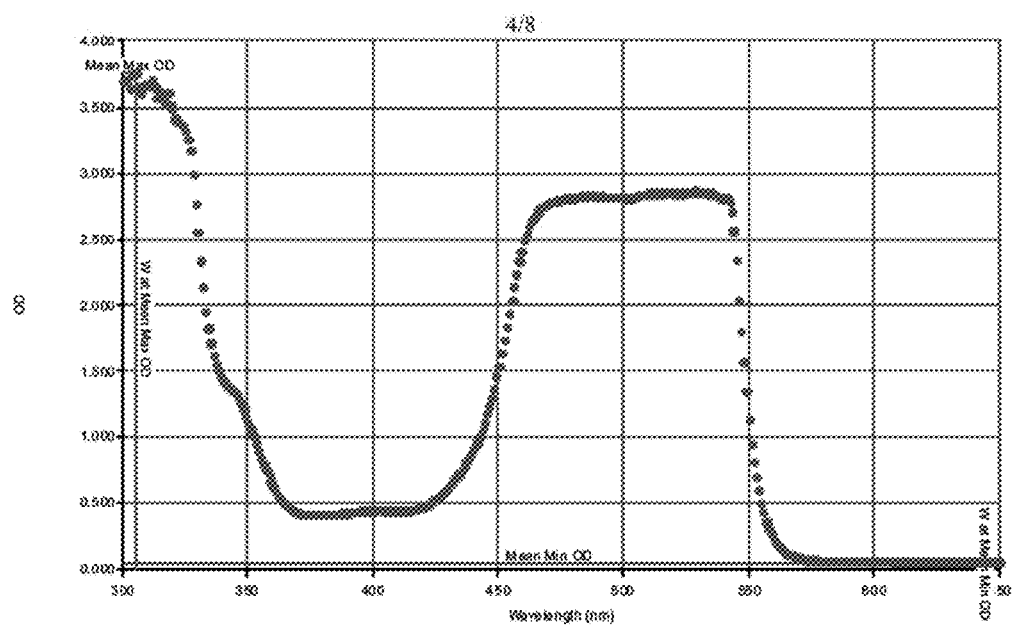
FIGS. 4a and 4b are absorbance and emission spectra, respectively, of an embodiment of the composition of the present invention which includes Eosin and Fluorescein (Example 1).
Figure 4B:
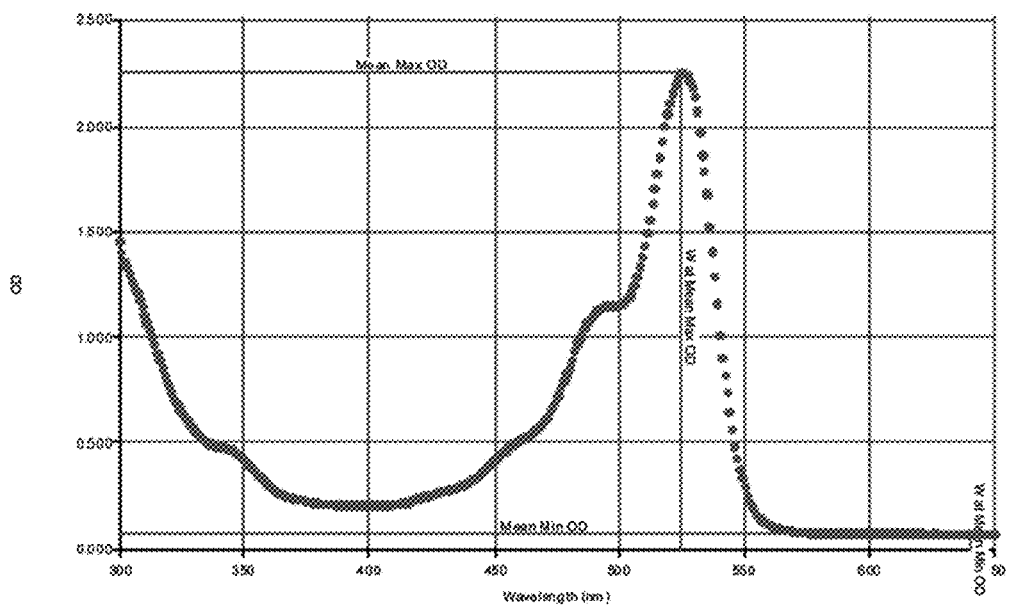

The photodynamic properties of the teeth whitening composition of Example 1 were evaluated using a flexstation 384 II spectrometer with the following parameters: mode fluorescence, excitation 460 nm, emission spectra 465-750 nm. The absorption and emission spectra are shown in FIGS. 4a and 4b.

Example 7

Figure 5A:
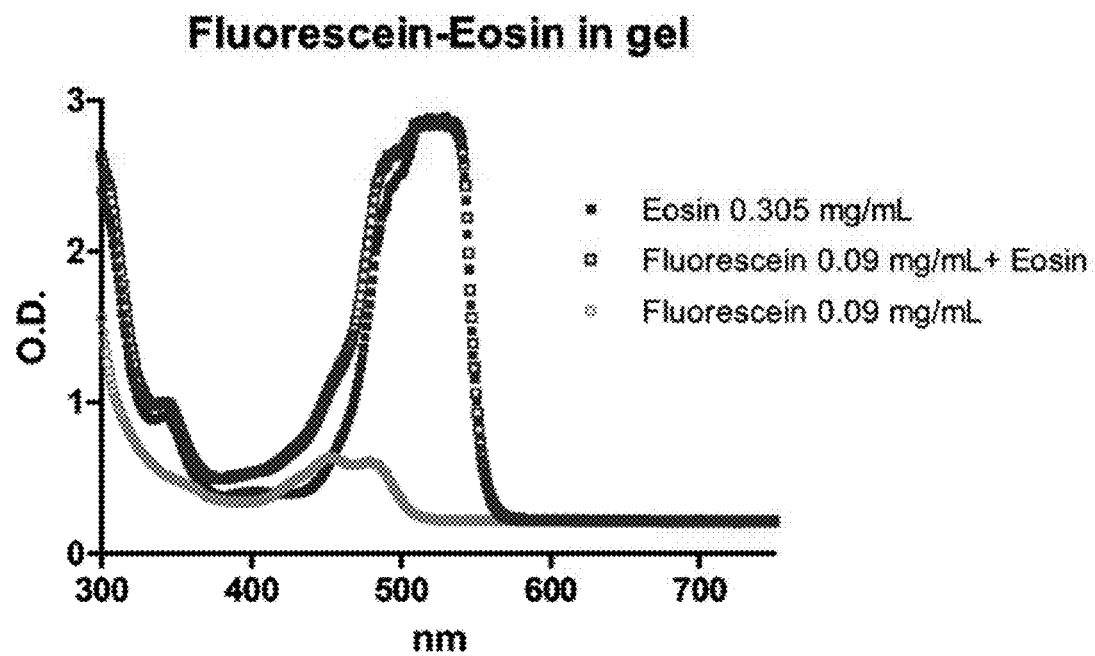
FIGS. 5a and 5b are absorbance and emission spectra, respectively, of an embodiment of the composition of the present invention which includes Eosin and Fluorescein in a 12% carbamide gel (Example 7).
Figure 5B:
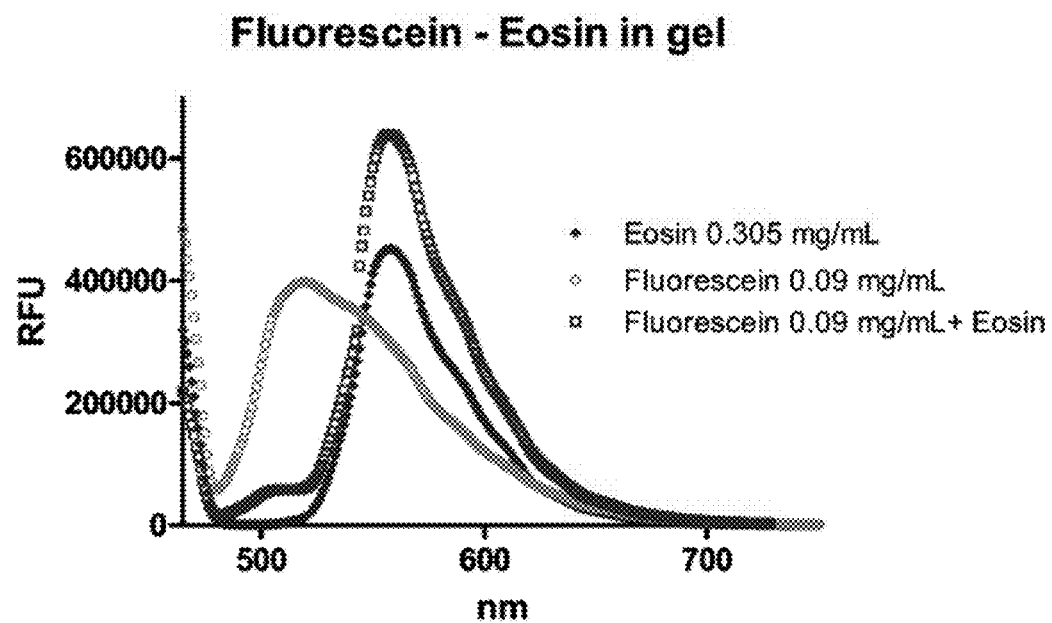

The photodynamic properties of (i) Fluorescein sodium salt at 0.09 mg/mL, (ii) Eosin Y at 0.305 mg/mL, and (iii) a mixture of Fluorescein sodium salt at 0.09 mg/mL and Eosin Y at 0.305 mg/mL in a 12% carbamide peroxide gel, were evaluated. A flexstation 384 II spectrometer was used with the following parameters: mode fluorescence, excitation 460 nm, emission spectra 465-750 nm. The absorption and emission spectra are shown in FIGS. 5a and 5b which shows a synergistic effect of the Eosin Y and Fluorescein combination.

Example 8

Figure 6A:
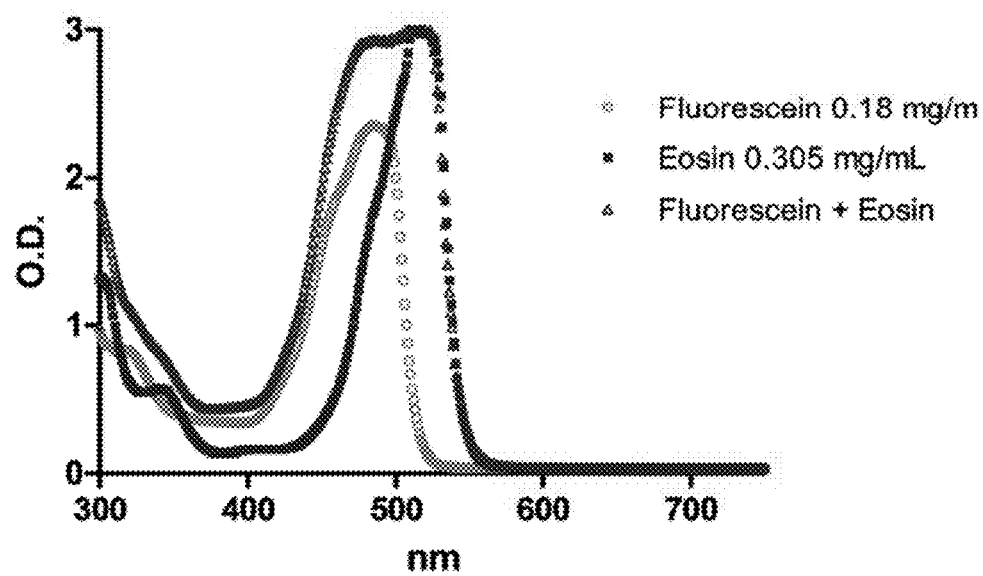
FIGS. 6a and 6b are absorbance and emission spectra, respectively, of an embodiment of the composition of the present invention which includes Eosin and Fluorescein in an aqueous solution (Example 8).
Figure 6B:
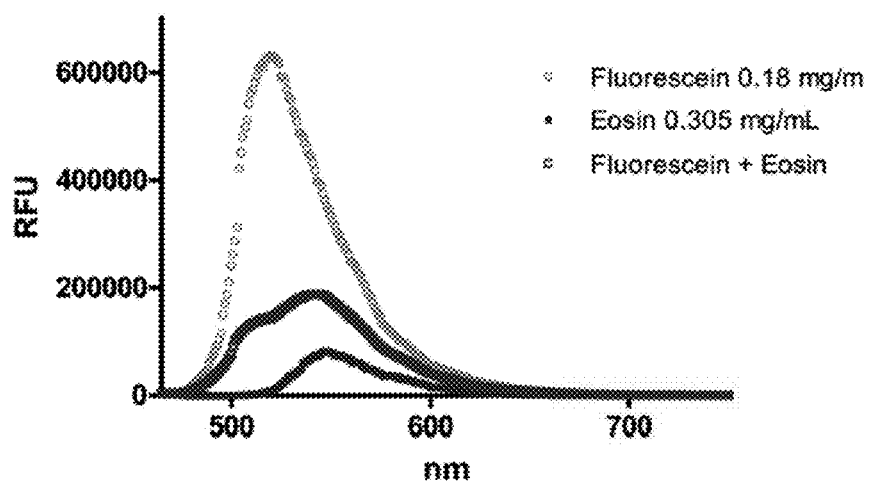

The photodynamic properties of (i) Fluorescein sodium salt at 0.18 mg/mL final concentration, (ii) Eosin Y at 0.305 mg/mL, and (iii) a mixture of Fluorescein sodium salt at 0.18 mg/mL and Eosin Y at 0.305 mg/mL in water containing Hyaluronic acid (25.4 µg/ml) and Glucosamine sulfate sodium (277.7 µg/mL), were evaluated. A flexstation 384 II spectrometer was used with the following parameters: mode fluorescence, excitation 460 nm, emission spectra 465-750 nm. The absorption and emission spectra are shown in FIGS. 6a and 6b which shows an unexpected synergy between the Eosin Y and Fluorescein components, in the absence of an oxidizing agent.

Example 9

Figure 7A:
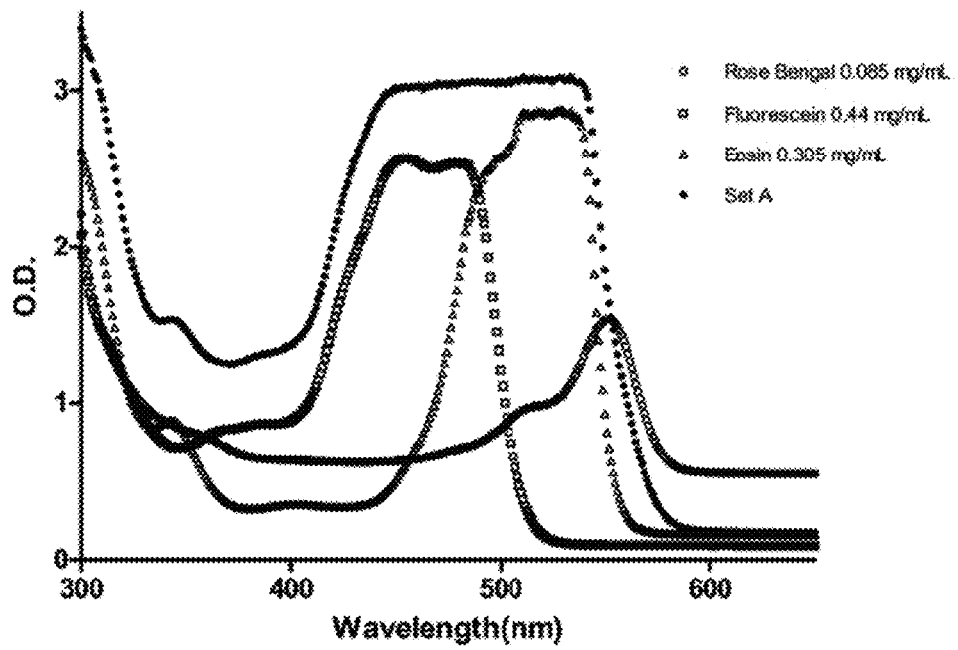
FIGS. 7a and 7b are absorbance and emission spectra, respectively, of an embodiment of the composition of the present invention which includes Eosin, Fluorescein and Rose Bengal in a 12% carbamide gel (Example 9).
Figure 7B:
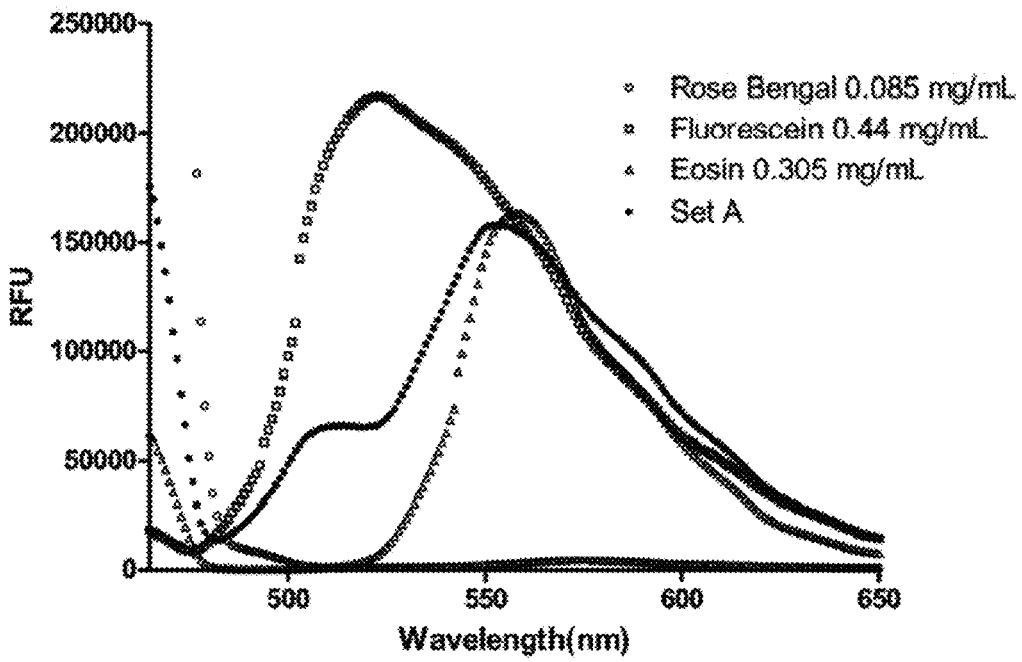

The photodynamic properties of (i) Rose Bengal 0.085 mg/mL, (ii) Fluorescein sodium salt at 0.44 mg/mL final concentration, (ii) Eosin Y at 0.305 mg/mL, and (iii) a mixture of (i), (ii) and (iii) in 12% carbamide peroxide gel, were evaluated. A flexstation 384 II spectrometer was used with the following parameters: mode fluorescence, excitation 460 nm, emission spectra 465-750 nm. The absorbance and emission spectra are shown in FIGS. 7a and 7b which show an unexpected synergy between the Rose Bengal, Eosin Y and Fluorescein components.

Example 10

Figure 8A:
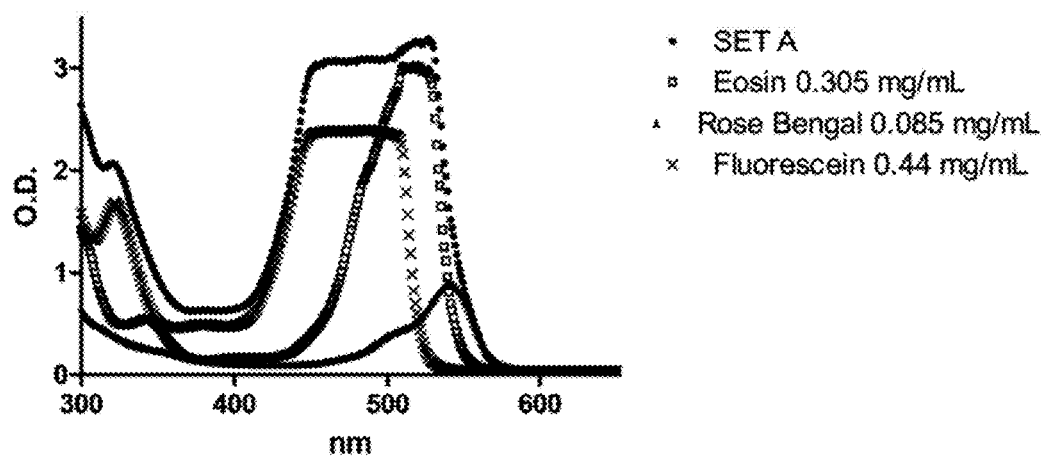
FIGS. 8a and 8b are absorbance and emission spectra, respectively, of an embodiment of the composition of the present invention which includes Eosin and Fluorescein in an aqueous solution (Example 10).
Figure 8B:
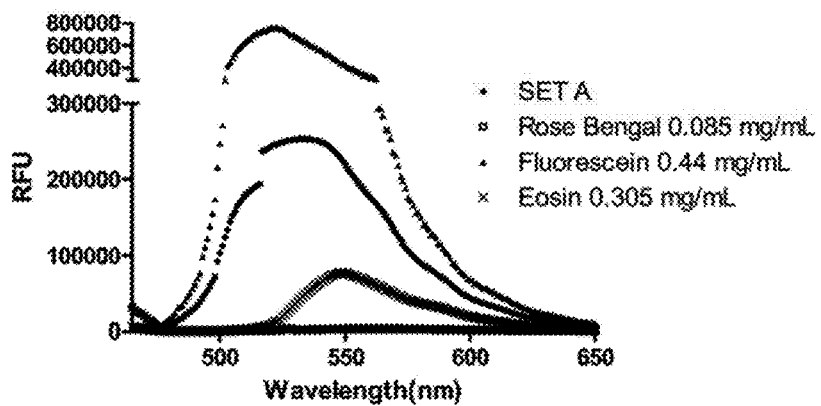

The photodynamic properties of (i) Rose Bengal 0.085 mg/mL, (ii) Fluorescein sodium salt at 0.44 mg/mL final concentration, (ii) Eosin Y at 0.305 mg/mL, and (iii) a mixture of (i), (ii) and (iii) in an aqueous solution, were evaluated. A flexstation 384 II spectrometer was used with the following parameters: mode fluorescence, excitation 460 nm, emission spectra 465-750 nm. The absorbance and emission spectra are shown in FIGS. 8a and 8b which show an unexpected synergy between the Rose Bengal, Eosin Y and Fluorescein components, in the absence of an oxidizing agent.

What is claimed is:

1. A method for whitening teeth comprising:
   applying a composition comprising an oxidizing agent and at least two chromophores to at least one tooth; and
   exposing the composition on the at least one tooth to actinic light;
   wherein the at least two chromophores comprise Fluorescein and Eosin Y, each in an amount of 0.001% to 1% by weight of composition.

2. The method of claim 1, wherein each of the at least one tooth is exposed to the actinic light for an amount of time selected from the group consisting of about 1 second to about 30 seconds, about 3 seconds to about 10 seconds, and about 5 seconds to about 10 seconds.

3. The method of claim 1, wherein the oxidizing agent is selected from a group consisting of hydrogen peroxide, carbamide peroxide, and a combination thereof.

4. The method of claim 3, wherein the hydrogen peroxide is less than or equal to 6% by weight of the composition.

5. The method of claim 3, wherein the carbamide peroxide is less than or equal to 22% by weight of the composition.

6. The method of claim 1, wherein the oxidizing agent is in an amount equivalent to a hydrogen peroxide content of about 6% by weight of the composition.

7. The method of claim 1, wherein the at least two chromophores further comprises a chromophore selected from a group consisting of Rose Bengal, Erythrosine, and any combination thereof.

8. The method of claim 1, wherein the composition further comprises a stabilizing agent, a thickening agent, a hydrophilic gelling agent, a base, or a combination thereof.

9. The method of claim 8, wherein the thickening agent is selected from a group consisting of silicon dioxide and fumed silica.

10. The method of claim 8, wherein the hydrophilic gelling agent is selected from a group consisting of polypropylene glycol, polyethylene glycol, propylene glycol, glycerol, a large molecular weight polyol, and a combination thereof.

11. The method of claim 8, wherein the base is potassium hydroxide.

12. The method of claim 1, wherein the pH of the composition is between 2 and 10.

13. The method of claim 1, wherein the at least two chromophores further comprises Rose Bengal.

14. The method of claim 13, wherein the Rose Bengal in an amount of 0.001% to 1% by weight of the composition.

15. The method of claim 1, wherein the at least two chromophores further comprises Erythrosine.

16. The method of claim 15, wherein the Erythrosine in an amount of 0.001% to 1% by weight of the composition.

* * * * *